United States Patent
Chandrasekaran et al.

(10) Patent No.: US 9,308,158 B2
(45) Date of Patent: Apr. 12, 2016

(54) TOOTHPASTE COMPRISING CALCIUM BASED ABRASIVES

(75) Inventors: Sembian Chandrasekaran, Mumbai (IN); Meenakshi Iyer, Mumbai (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/128,865

(22) PCT Filed: Jul. 4, 2012

(86) PCT No.: PCT/EP2012/063028
§ 371 (c)(1),
(2), (4) Date: Dec. 23, 2013

(87) PCT Pub. No.: WO2013/007571
PCT Pub. Date: Jan. 17, 2013

(65) Prior Publication Data
US 2014/0127143 A1    May 8, 2014

(30) Foreign Application Priority Data

Jul. 12, 2011   (IN) .................. 1999/MUM/2011

(51) Int. Cl.
*A61Q 11/00* (2006.01)
*A61K 8/19* (2006.01)
*A61K 8/81* (2006.01)
*A61K 8/26* (2006.01)

(52) U.S. Cl.
CPC ............... *A61K 8/8129* (2013.01); *A61K 8/19* (2013.01); *A61K 8/26* (2013.01); *A61K 8/8164* (2013.01); *A61Q 11/00* (2013.01)

(58) Field of Classification Search
CPC . A61Q 11/00; A61K 8/8164; A61K 2800/92; A61K 2300/00
See application file for complete search history.

(56) References Cited

U.S. PATENT DOCUMENTS

| | | | |
|---|---|---|---|
| 4,081,526 A | 3/1978 | Asakawa et al. | |
| 4,296,096 A * | 10/1981 | Pierce | 424/52 |
| 4,992,258 A | 2/1991 | Mason | |
| 5,192,529 A | 3/1993 | Garlick, Jr. et al. | |
| 5,236,696 A | 8/1993 | Catiis et al. | |
| 6,258,342 B1 | 7/2001 | Harcum et al. | |
| 6,569,408 B1 | 5/2003 | Yue et al. | |
| 2004/0131560 A1 | 7/2004 | Corcoran et al. | |
| 2005/0214720 A1 * | 9/2005 | Milanovich et al. | 433/215 |
| 2006/0275224 A1 | 12/2006 | Burnet et al. | |
| 2007/0025928 A1 | 2/2007 | Glandorf et al. | |
| 2007/0122359 A1 | 5/2007 | Wang et al. | |
| 2010/0254915 A1 | 10/2010 | Kao | |
| 2010/0316580 A1 * | 12/2010 | Kohli et al. | 424/52 |

FOREIGN PATENT DOCUMENTS

| | | |
|---|---|---|
| EP | 0525913 | 2/1993 |
| EP | 1935395 A1 | 6/2008 |
| WO | WO2007063507 | 6/2007 |
| WO | WO2008041055 A1 | 4/2008 |
| WO | WO2008068323 A1 | 6/2008 |
| WO | WO2009134657 A1 | 11/2009 |

OTHER PUBLICATIONS

International Search Report, PCT/EP2012/063028, mailed Apr. 4, 2013, 4 pp.
IPRP2 in PCTEP2012063028, Jan. 3, 2014.
Written Opinion in PCTEP2012063028, Apr. 4, 2013.

* cited by examiner

*Primary Examiner* — Robert A Wax
*Assistant Examiner* — Tracy Liu
(74) *Attorney, Agent, or Firm* — Greenberg Traurig, LLP

(57) ABSTRACT

It has been found that toothpastes containing balance amounts of calcium based abrasive, copolymer of vinylmethylether and maleic acid and clay have significantly better stability even at elevated temperature. It has also been determined that the selected combination allows for complete removal of or at least a significant reduction in thickening silica, with almost no adverse effect on rheology. Disclosed is a toothpaste composition comprising: (i) a calcium based abrasive; (ii) a copolymer of vinylmethyl ether and maleic acid; and (iii) a clay, wherein ratio of the calcium based abrasive to said copolymer of vinylmethyl ether and maleic acid is at least 1:0075 and ratio of said calcium based abrasive to said clay is at least 1:0.02.

8 Claims, No Drawings

TOOTHPASTE COMPRISING CALCIUM BASED ABRASIVES

FIELD OF INVENTION

The present invention relates to toothpastes containing Calcium based abrasive.

BACKGROUND AND RELATED ART

Toothpastes are generally of two types; opaque and transparent. Opaque toothpastes are generally white. They may also be coloured. Such toothpastes usually contain Calcium based abrasives; particularly chalk. Gel toothpastes usually contain abrasive silica. Multiphase toothpastes which have an opaque phase and a transparent phase are also known.

Toothpastes, particularly the chalk based ones, generally also contain thickening silica. It helps build viscosity. However, thickening silica, especially at higher levels, may adversely affect flavour delivery. This often compels formulators to dose an appropriate overage of flavour. Flavours are very expensive. Therefore even slight reduction in flavour can be economically significant. Therefore, it is desirable either to reduce the level of thickening silica, or preferably, have no thickening silica.

Toothpastes usually contain some polymers. Cellulosic polymers such as Sodium carboxymethyl cellulose (SCMC) are included as thickeners. Polymers of vinylmethyl ether and maleic acid, e.g. some polymers of the GANTREZ® family (GANTREZ® is registered trademark of International Specialty Products Inc (ISP)) are often used in toothpastes containing chalk. Known art indicates that such polymers are used for delivery of flavour.

One of the disadvantages of polymers of vinylmethyl ether and maleic acid, especially in toothpastes containing Calcium based abrasives is that unbalanced amount of such polymers can affect spreadability of the paste. Further, the paste becomes unstable after about a month of storage at elevated temperature. An arbitrary reduction in the level of such polymers cannot be a viable solution as it may adversely affects delivery of flavour.

Known art suggests using a combination of certain thickening polymers to solve some or all of the problems described earlier.

WO08041055 A1 (Procter & Gamble) discloses some examples of toothpaste compositions thickened with a material selected from xanthan gum, CMC, Gantrez® and carrageenan, albeit without explaining any technical effect of the combination of binders.

WO09134657 A1 (Procter & Gamble) describes toothpastes thickened with selected carrageenans, additionally having one or more of carboxyvinyl polymers, hydroxyethyl cellulose (HEC), natural and synthetic clays (e.g., VEE-GUM® and LAPONITE®), CMC, SCMC, gum karaya, xanthan gum, gum arabic, gum tragacanth, colloidal magnesium aluminium silicate and finely divided silica. Disclosed toothpastes spread easily in the mouth. The toothpastes exhibit increased dispersibility in saliva during use, which provides for increased contact time of the composition with the user's teeth and oral cavity tissues such that the active dental agents are more rapidly available for beneficial activity.

WO2008068323 A1 (GLAXO GROUP LTD) discloses dentifrice compositions having a first thickening agent which is xanthan gum, a second thickening agent which is carrageenan and/or a polyacrylic acid and a third thickening agent which is thickening silica. Carrageenan and/or polyacrylic acid is said to reduce stringiness.

WO2007063507 A2 (Procter & Gamble) discloses dentifrice compositions containing a binder system made of:
 (i) a hydrophilic clay material (e.g. LAPONITE®, CAB-O-SIL®)
 (ii) a modified cellulose polymer, e.g., SCMC (such as BLANOSE® OPTICEL® 100, and AQUALON®), polyvinylpyrrolidone and HEC;
 (iii) a carboxyvinyl polymer such as CARBOPOL® series and ULTREZ® 10; and,
 (iv) a natural gum derived anionic polymer such as carrageenan, xanthan gum, gellan gum, and locust bean gum.

The binder system swells or thickens in presence of polar solvent. Disclosed binder system provides good rheology at lower amounts of each binder, and thereby helps reduce costs.

EP0525913 A1 (Colgate-Palmolive, 1993) discloses viscoelastic toothpastes thickened with GANTREZ® type of polymers. Disclosed compositions have good stability against phase separation or syneresis, viscosity change in storage, and settling of dissolved, dispersed or suspended particles under high and low temperature conditions, freedom from fish eyes, texture and other cosmetic properties, ease of extrusion from a dispensing tube, pump or the like (easily shear thinned), good stand-up after extrusion (quick recovery of structure).

U.S. Pat. No. 5,192,529 A (Unilever, 1993) discloses a dentifrice composition thickened with carboxymethyl cellulose and hydroxylethyl cellulose in the range of 1:5 to 5:1. Disclosed compositions have low stringiness, good phase stability and proper texture.

We have determined that toothpastes having selective balance between a Calcium based abrasive, a copolymer of vinylmethylether and maleic acid and a clay have significantly better stability, even after being stored at elevated temperature. We have also determined that this also allows for complete removal of, or at least a significant reduction in thickening silica, with almost no adverse effect on rheology. In general, thickening silica is very commonly used in toothpastes.

SUMMARY OF THE INVENTION

In a first aspect, disclosed is a toothpaste composition comprising:
 (i) a calcium based abrasive;
 (ii) a copolymer of vinylmethyl ether and maleic acid; and,
 (iii) a clay,
wherein ratio of the calcium based abrasive to said copolymer of vinylmethyl ether and maleic acid is at least 1:0075 and ratio of said calcium based abrasive to said clay is at least 1:0.02.

In a second aspect, disclosed is a method of promoting oral hygiene which includes a step of applying to the teeth, an effective amount of a toothpaste composition of the first aspect.

In a third aspect, disclosed is use of a toothpaste composition of the first aspect for oral hygiene.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

It should be noted that in specifying any range of concentration or amount, any particular upper concentration can be associated with any particular lower concentration or amount.

DETAILED DESCRIPTION

For better understanding of the invention; reference should be made to the following detailed description of preferred embodiments.

The Calcium Based Abrasive

All toothpastes contain an abrasive. Gels usually contain silica, whereas opaque creams generally contain Calcium based abrasives, especially chalk.

Preferred toothpaste compositions have 5 to 60 wt % calcium based abrasive. In more preferred compositions it is 30 to 60 wt % and further more preferably from 35 to 55 wt %. Optimal compositions have 40 to 55 wt % Calcium based abrasive.

A preferred abrasive is Fine ground natural chalk (FGNC), which is a form of chalk. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling.

FGNC may be used as the sole Calcium based abrasive. However, FGNC may also be used with the other Calcium based abrasives for some balance of abrasion. Usually the particle size of chalk is from 1 to 60 µm, and preferred sizes range from 1 to 15 µm.

Other preferred Calcium based abrasives include dicalcium phosphate (DCP), calcium pyrophosphate and precipitated calcium carbonate (PCC), which preferably are included at 25 to 55 wt %, more preferably 35 to 50 wt %.

When a combination of Calcium based abrasives is desired, it is preferred that FGNC is 35 to 100%, more preferably 75 to 100% and especially from 95 to 100% of the total amount of Calcium based abrasives. In such cases, the balance, most preferably, is PCC.

Other abrasives may also be used depending upon the intended degree of abrasion. These include synthetic abrasive polishing agents such as amorphous precipitated silica and silica gels. Other abrasive agents include magnesium carbonate, sodium metaphosphate, potassium metaphosphate, zirconium silicate, potassium metaphosphate, magnesium orthophosphate, tricalcium phosphate, magnesium orthophosphate, trimagnesium phosphate, aluminum silicate, zirconium silicate and perlite.

The Copolymer of Vinylmethylether and Maleic Acid

Preferred are 1:4 to 4:1 copolymers of maleic acid with methylvinyl ether having molecular weight (MW) of 30,000 Daltons to 1,000,000 Daltons, most preferably 30,000 Daltons to 500,000 Daltons. These copolymers are available for example as GANTREZ® series. Particularly preferred copolymers include GANTREZ® S-96 and GANTREZ® S-97, which are available in powder and solution forms. When the solution form is used, an appropriately calculated higher amount may be added so that the level of the active ingredient may be maintained. Preferred toothpaste compositions include 0.1 to 2 wt % copolymer of vinylmethylether and maleic acid. More preferred compositions include 0.3 to 0.8 wt % copolymer and most preferred compositions include 0.3 to 0.6 wt % copolymer.

Copolymers of vinylmethyl ether and maleic acid are well-known for delivery of actives, especially TRICLOSAN®.

It is believed that such copolymers anchor to the teeth. The copolymers are used widely in gel toothpastes, but their use along with Calcium based abrasives has been limited because the polymers chelate and precipitate Calcium ions. Toothpastes containing a copolymer of vinylmethylether and maleic acid alone were found to be rubbery. Higher amount of such copolymers made the compositions rubbery, whereas lower amounts lead to compositions that were lesser adapted for delivery of actives and flavour.

Clay

The composition contains a clay. A preferred clay is smectite clay, which may be chosen from aluminium silicates such as the montmorillonites (bentonites, hectorites and derivatives thereof); purified magnesium aluminium silicates (various grades are commercially available as VEEGUM® from R. T. Vanderbilt Company); purified sodium magnesium silicates (commercially available as LAPONITE® in various grades); organically modified smectites including tetra alkyl and/or trialkyl ammonium smectites (organically modified montmorillonite clays) such as quaternium-18 bentonite, quaternium-18 hectorite, stearalkonium bentonite and stearalkonium hectorite/and mixtures thereof. Smectites constitute a group in the class of natural aluminosilicate minerals known as phyllosilicates or layered silicates. Other groups in this class include micas, kaolins, vermiculites, chlorites, talc and pyrophyllite.

A preferred smectite clay is VEEGUM® HV.

Preferred toothpaste compositions include 0.2 to 3 wt % clay. More preferred compositions include 0.5 to 1 wt % clay.

Without wishing to be bound by theory it is believed that the clay, particularly smectite clay, prevents, or at least significantly reduces tendency of the copolymer of vinylmethylether and maleic acid to precipitate Calcium ions.

Therefore the clay allows the copolymer of vinylmethyl ether and maleic acid to deliver flavour and actives.

Other Preferred Ingredients

In addition to the ingredients described earlier, preferred compositions may include one or more other ingredients commonly found in toothpaste compositions.

Gum

Preferred toothpaste compositions include a gum. Cellulose based gums are especially preferred. Preferred cellulose based gums may be selected from cellulose ethers, which include hydroxyethyl cellulose (HEC), hydroxypropyl cellulose (HPC), ethylhydroxyethyl cellulose (EHEC), carboxymethyl cellulose (CMC), carboxymethylhydroxyethyl cellulose (CMHEC), hydroxypropylhydroxyethyl cellulose (HPHEC), methyl cellulose (MC), methylhydroxypropyl cellulose (MHPC), methylhydroxyethyl cellulose (MHEC), carboxymethylmethyl cellulose (CMMC), hydrophobically modified carboxymethyl cellulose (HMCMC), hydrophobically modified hydroxyethyl cellulose (HMHEC), hydrophobically modified hydroxypropyl cellulose (HMHPC), hydrophobically modified ethylhydroxyethyl cellulose (HMEHEC), hydrophobically modified carboxymethylhydroxyethyl cellulose (HMCMHEC), hydrophobically modified hydroxypropylhydroxyethyl cellulose (HMHPHEC), hydrophobically modified methyl cellulose (HMMC), hydrophobically modified methylhydroxypropyl cellulose (HMMHPC), hydrophobically modified methylhydroxyethyl cellulose (HMMHEC), and hydrophobically modified carboxymethylmethyl cellulose (HMCMMC).

Other celluloses include cationic hydroxyethyl cellulose (cationic HEC), cationic hydrophobically modified hydroxyethyl cellulose (cationic HMHEC) and microcrystalline cellulose.

A highly preferred gum is Sodium carboxymethyl cellulose (SCMC). Particularly preferred sodium carboxymethyl celluloses include those with degree of substitution of from 0.6 to 0.99, preferably from 0.7 to 0.95. Further, preferred SCMCs include those with viscosity of 250 mPa·s to 10000 mPa·s as measured on a Brookfield viscometer TA spindle at 30 rpm, 23° C. and reading after 30 seconds when slurried with flavour in a 1:1 ratio.

A preferred gum may also be guar gum or its derivative. Such derivatives include carboxymethyl guar (CM guar), hydroxyethyl guar (HE guar), hydroxypropyl guar (HP guar), carboxymethylhydroxypropyl guar (CMHP guar), cationic guar, hydrophobically modified guar (HM guar), hydrophobically modified carboxymethyl guar (HMCM guar), hydrophobically modified hydroxyethyl guar (HMHE guar), hydrophobically modified hydroxypropyl guar (HMHP guar), cationic hydrophobically modified hydroxypropyl guar (cationic HMHP guar), hydrophobically modified carboxymethylhydroxypropyl guar (HMCMHP guar) and hydrophobically modified cationic guar (HM cationic guar).

Other preferred gums include xanthan gum, carrageenan and derivatives, such as Irish moss and viscarin, gellan gum, sclerotium gum and derivatives, pullulan, rhamsan gum, welan gum, konjac, curdlan, algin, alginic acid, alginates and derivatives, starch phosphate derivatives, agar and derivatives, gum arabic and derivatives, pectin and derivatives, chitosan and derivatives, resinous polyethylene glycols such as PEG-XM where X is greater than or equal to 1, karaya gum, locust bean gum, natto gum, tragacanth gum, chitin derivatives, gelatin, betaglucan, dextrin, dextran, cyclodextrin and polyquaterniums. Other gums include furcellaren gum, ghatti gum, psyllium gum, quince gum, tamarind gum, larch gum, and tara gum.

Preferred compositions include 0.1 to 2 wt %, more preferably 0.3 to 1.5 wt % gum.

Other Thickening Agents

Preferred toothpaste compositions may also include one or more other thickening agents such as carboxyvinyl polymers which include carbomers which are commercially available from B. F. Goodrich as the CARBOPOL® series, including CARBOPOL® 934, 940, 941 and 956. Other preferred grades include acrylates/$C_{10-30}$ alkyl acrylate crosspolymers which are commercially available as ULTREZ® 21, PEMULEN® TR-1, and PEMULEN® TR-2, from Noveon Corporation. Preferred compositions may include 0.05 to 10 wt %, more preferably 0.1 to 5 wt %, and even more preferably 0.25 to about 4 wt % of other thickening agents.

Thickening Silica

Gel toothpastes generally contain up to 8.5 wt % thickening silica whereas opaque toothpastes typically contain 3 to 4 wt % thickening silica. The adverse effects of thickening silica on flavour release are well known. Described invention permits complete elimination of, or at least a significant reduction in thickening silica; thereby allowing for enhanced flavour delivery. This represents a significant technical advancement and economic significance over the state of the art. Preferred toothpaste compositions may include up to 2 wt % thickening silica. Further preferred compositions have 1.5 wt %, or even less than 1 wt % thickening silica. Optimal compositions may have less than 0.5 wt % thickening silica. Highly preferred compositions are free of thickening silica.

When present, preferred thickening silicas include AEROSIL® T series from Degussa or the CAB-O-SIL® series from Cabot Corporation, silica gels such as the SYLODENT® or SYLOX® series from W. R. Grace & Co or precipitated silica such as ZEOTHIX® 265 from J. M. Huber Corporation.

Useful silica thickeners also include ZEODENT® 165, ZEODENT® 163 and/or 167 and ZEOFREE® 153, 177, and/or 265 silicas, all available from J. M. Huber Corporation. Other preferred thickening silicas include MFIL®, MFIL®-P (From Madhu Silica, India), SIDENT® 22 S and AEROSIL® 200 (Ex. Evonik Industries), SYLODENT® and PERKASIL® thickening silicas from WR Grace & Company and Tixosil® 43 and 331 from Rhodia, synthetic finely divided pyrogenic silica such as those sold under the trademarks SYLOID® 244, SYLOID® 266 and AEROSIL® D-200.

Bicarbonate

Preferred compositions may include 0.5 to 50 wt %, preferably from about 0.5 to 30 wt %, more preferably from about 2 to 20 wt %, and most preferably from about 5 to 18 wt % of an alkali metal bicarbonate salt.

De-Sensitising Agents

A de-sensitising agent is a potassium salt selected from potassium nitrate, potassium chloride, potassium citrate, potassium tartrate and potassium acetate used preferably from 0.5 to 3 wt %, more preferably from 1 to 2.5 wt % and especially from 1.7 to 2.2 wt %. Some anti-sensitive agents may also thicken the compositions.

Silicate

Preferred toothpaste compositions may include an alkali metal silicate. The alkali metal is sodium or potassium, preferably sodium. Sodium silicate is generally available as 10 to 40% aqueous solution, most common being 30% solution. Sodium silicate is available as neutral sodium silicate or alkaline sodium silicate. Preferred toothpastes have neutral sodium silicate. Sodium silicate is available with varying ratios of $Na_2O:SiO_2$.

Sodium silicate with $Na_2O:SiO_2$ ratio in the range of 3.0 to 3.8 is preferred, more highly preferred range being 3.25 to 3.5. Preferred toothpastes include 0.1 to 5 wt % silicate (on dry weight basis). Thus, a 30% solution of sodium silicate is added to the composition in an amount in the range of 0.3 to 16 wt %.

Anti-Caries Agent

Preferred compositions may include one or more anti-caries agent. Such agents are typically fluorides. It is preferred that the source of fluoride is an alkali-metal salt of monofluorophosphoric acid, preferably sodium monofluorophosphate (SMFP). SMFP is the fluoride source of choice when it comes to toothpaste compositions having Calcium based abrasives, especially chalk; since the alternative, sodium fluoride, reacts with the calcium carbonate to form insoluble calcium fluoride which has limited anti-caries activity. Preferred compositions include 0.01 to 2 wt %, more preferably 0.15 to 1 wt % and especially preferably 0.2 to 0.5 wt % anti-caries agent. It is preferable to maintain the free fluoride ion concentration from 100 to 2000 ppm, preferably from 900 to 1500 ppm. Other preferred anti-caries agents include sodium- and stannous fluoride, aminefluorides, sodium trimetaphosphate and casein.

Zinc Salts

Zinc salts are effective antimicrobial agents. Useful Zinc salts include zinc chloride, zinc sulphate, zinc nitrate, zinc citrate, zinc gluconate, zinc acetate, zinc lactate and zinc salicylate. Mixed salts such as sodium zinc citrate can also be used. Other preferred zinc salts include zinc salts of organic acids such as zinc citrate, zinc lactate, zinc maleate, zinc salicylate, zinc gluconate and zinc ascorbate. However, the most preferred salt is Zinc sulphate. Mixtures of different zinc salts can be used. When present, the zinc salt is preferably included from 0.1 to 5 wt % and preferably 0.1 to 2 wt % and most preferably, the Zinc salt is 0.1 to 0.5 wt %.

Excess Zinc will lead to unacceptable taste and higher level of astringency and may be incompatible with other ingredients leading to precipitation, especially of anionic polymers, when present.

Humectants

Humectants enhance flavour, prevent harsh taste and provide a fresh and pleasant sensation in the mouth. They also prevent caking. A humectant serves to keep the dentifrice compositions from hardening upon exposure to air and also imparts some sweetness to the formulations to further minimize the astringency ascribed to the Zinc salt. Preferred levels are from 10 to 70 wt %, more preferably about 25 to 60 wt % by weight. Typical humectants include sorbitol (generally available as 70% aqueous solution), glycerine, maltitol and xylitol. More preferred toothpastes contain 16 to 30 wt % glycerine. Sorbitol solution supplies sweetness and body to the composition and gives a desirable mouth feel. It may be preferable to use a mixture of glycerine and sorbitol for lubricated mouth feel.

Antibacterial Agent

Preferred compositions may include an anti-bacterial agent, which may be Stannous salts such as Stannous pyrophosphate. Further examples of anti-bacterial agents include quaternary ammonium compounds such as cetylpyridinium chloride; bis-biguanides such as chlorhexidine, chlorhexidine digluconate, hexetidine, octenidine, alexidine, TRICLOSAN® and other halogenated bisphenolic compounds such as 2,2' methylenebis-(4-chloro-6-bromophenol). A particularly preferred antibacterial agent is TRICLOSAN®.

Preservatives

Toothpastes containing Calcium based abrasives, especially chalk; are prone to bacterial growth. Certain preservatives, e.g. methyl, ethyl, butyl, propyl and isopropyl esters of parahydroxybenzoic acid may be particularly useful against bacterial growth. A mixture of methyl, ethyl, butyl and propyl esters of parahydroxybenzoic acid is particularly preferred. The activity of this mixture can be enhanced by adding phenoxyethanol. Formaldehyde and dimethyl hydantoin are other preferred preservatives. Preservatives are generally included at 0.05 to 0.8 wt %.

Antioxidants

Preferred antioxidants are those which are compatible with other components and are not hazardous to health. These include ascorbic acid, ascorbyl palmitate, thiodipropionic acid, calcium ascorbate, dilauryldithiopropionate, gum guaiac, sodium ascorbate, butylated hydroxyl toluene, butylated hydroxyl anisole, and tocopherols. Mixtures of antioxidants can be used.

When present, the antioxidant is added in a level effective to reduce or mitigate discoloration that would otherwise result from oxidation of the components of the toothpastes. Preferred levels are from 0.01 to 1 wt %.

Surfactants

Toothpastes generally contain surfactants, also commonly referred to as sudsing agents. Suitable surfactants are those which are reasonably stable and provide foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Nonionic surfactants can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), POLYOXYL® 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The nonionic surfactant Poloxamer® 407 is one of the most preferred surfactant because the poloxamer has been discovered to help reduce astringency.

Useful amphoteric surfactants can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Preferred levels are from 0.25 to 12 wt %, preferably from 0.5 to 8 wt %, and most preferably from 1 to about 6 wt %.

Sweetening Agents

Toothpastes may also contain a sweetening agent. Preferred sweetening agents include sodium saccharin, aspartame, sucralose, thaumatin, acesulfame potassium, stevioside, stevia extract, paramethoxy cinnamic aldehyde, neohesperidyl dihydrochalcone and perillartine. Other preferred sweeteners include dextrose, polydextrose, sucrose, maltose, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, neotame, saccharin and salts thereof, sucralose, dipeptide-based intense sweeteners, cyclamates, dihydrochalcones, and mixtures thereof. Typical levels are from 0.005 to 5 wt %, more preferably from 0.01 to 1 wt %. Some sweeteners may also serve as humectants.

Foam Modulators

Useful foam modulators include polyethylene glycols (PEGs), also known as polyoxyethylenes. High molecular weight PEGs are suitable, including those having an average molecular weight of 200,000 to 7,000,000 Daltons, for example 500,000 to 5,000,000 Daltons or 1,000,000 to 2,500,000 Daltons. Preferred compositions include 0.1 to 10 wt %, more preferably 0.2 to 5 wt %, and most preferably 0.25 to 2 wt % foam modulator.

Other Common Ingredients

Preferred toothpastes may include one or more bleaching agents such as peroxy compounds e.g. potassium peroxydiphosphate, effervescing systems such as sodium bicarbonate/citric acid systems, colour change systems, and chelating agents from 0.001 to 6 wt %, preferably at from 0.5 to 4 wt %, which include alkali metal salts of citric acid, alanine, glycine and serine.

The most preferred are the alkali metal salts of citric acid, especially potassium citrate and most preferably tri-potassium citrate.

Liposomes may also be used to improve delivery or stability of one or more active ingredients. Preferred compositions may also include one or more of breath strips, sparkles, large silica particles, granules, beads, and flavour encapsulates for enhanced sensory benefits or for visual appeal.

Titanium dioxide may also be added for opacity. Titanium dioxide is generally added from 0.25 to 5 wt %.

Colouring agents may also be added. The colouring agent may be in the form of an aqueous solution, preferably 1% colouring agent in a solution of water.

A flavour system can also be included. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants are the paramenthane carboxyamide agents such as N-ethyl-p-menthan-3-carboxamide (known commercially as "WS-3®") and mixtures thereof. The flavour is generally from 0.001 to 5 wt %.

Physical Properties

Viscosity of preferred toothpaste compositions is 80,000 to 500,000 cps, when measured at 1/s and 25° C. with a BROOKFIELD® Viscometer using T-bar D-spindle at 5 rpm (revolutions per minute). Viscosity of more preferred toothpaste compositions is 100,000 to 200,000 cps.

The pH of preferred compositions is up to 10.5. Preferably, the pH is less than 9.5. The invention will now be explained with the help of non-limiting exemplary embodiments.

EXAMPLES

Example-1

Opaque white toothpastes having different types and amounts of thickeners were made by well known method.

Formulations of the toothpastes are described in table 1. After making the toothpastes, they were stored at 45° C. for one month, after which their stability was checked.

Interpretation of the Data in Table 1

Composition-1 having 2 wt % GANTREZ® and 3.75 wt % thickening silica was rubbery. This was believed to be because of high level of GANTREZ® S-97. When GANTREZ® was reduced to 0.5 wt % in Composition-2, the composition was acceptable when made, but turned rubbery after storage. This indicates that reduction in GANTREZ® did not solve the technical problem. Composition 3 was made without thickening silica. However, this composition was also found to be unstable, and so were compositions 4 and 5. Only the preferred compositions 6 and 7 having selective balance between the Calcium based abrasive, the copolymer of vinylmethyl ether and maleic acid, and the clay were stable.

Example-2

Release of Triclosan in Saliva

Triclosan (TCN) is a very common antibacterial agent. Efficacy of triclosan is directly proportional to its concentration in saliva at the time of brushing. However, efficacious quantity of triclosan may not be released into the saliva even with toothpaste containing triclosan. It is generally believed that calcium inhibits this release.

We observed a significantly higher release of triclosan while comparing efficacy of a preferred composition against marketed antibacterial toothpaste having triclosan (0.3 wt %) and calcium carbonate (chalk) but no copolymer of vinylmethyl ether and maleic acid.

TABLE 1

| Ingredients/wt % | Composition | | | | |
|---|---|---|---|---|---|
| | 1 | 2 | 3 | 4 | 5 |
| Water | 30 | 32 | 30 | 28 | 25 |
| VEEGUM ® HV | — | — | — | 0.8 | 0.8 |
| Sorbitol (70%) | 15 | 15 | 15 | 15 | 15 |
| FGNC | 40 | 40 | 45 | 45 | 50 |
| MFIL ® | 3.75 | 3.75 | — | 1.5 | — |
| SCMC | 0.625 | 0.625 | 0.9 | 0.45 | 0.45 |
| GANTREZ ® S-97 | 2 | 0.5 | 0.8 | 0.75 | 0.75 |
| Sodium lauryl sulphate | 2.5 | 2.5 | 2.5 | 2.5 | 2.5 |
| Sodium Silicate (30%) | 1.75 | 1.75 | 1.75 | 1.75 | 1.75 |
| Flavour | 0.2 | 0.2 | 0.2 | 0.2 | 0.2 |
| Other minors to* | 100 | 100 | 100 | 100 | 100 |
| Viscosity/cps | gummy | 184,000 | 136,000 | 130,000 | 152,000 |
| Ratio of FGNC to GANTREZ ® S-97 | 1:0.05 | 1:0.0125 | 1:0.0175 | 1:0.0166 | 1:0.015 |
| Ratio of FGNC to VEEGUM ® | — | — | — | 1:0.0177 | 1:0.016 |
| After storage | rubbery | rubbery | rubbery | rubbery | rubbery |

| Ingredients/wt % | Composition | |
|---|---|---|
| | 6 | 7 |
| Water | 34 | 34 |
| VEEGUM ® HV | 0.8 | 0.8 |
| Sorbitol (70%) | 15 | 15 |
| FGNC | 40 | 40 |
| MFIL ® | 1.5 | 1.5 |
| SCMC | 0.45 | 0.45 |
| GANTREZ ® S-97 | 0.3 | 0.75 |
| Sodium lauryl sulphate | 2.5 | 2.5 |
| Sodium Silicate (30%) | 1.75 | 1.75 |
| Flavour | 0.2 | 0.2 |
| Other minors to* | 100 | 100 |
| Ratio of FGNC to GANTREZ ® S-97 | 1:0.0075 | 1:0.0187 |
| Ratio of FGNC to VEEGUM ® | 1:0.02 | 1:0.02 |
| Viscosity/cps | 82,400 | 100,000 |
| After storage | stable | stable |

*this includes TRICLOSAN ®, preservative, benzyl alcohol, colour, pigments and sachharin.

Formulation of the tested preferred composition is shown in table-2.

TABLE 2

| Ingredients/wt % | Composition 8 |
| --- | --- |
| Water | 28 |
| VEEGUM ® HV | 0.8 |
| sorbitol (70%) | 15 |
| FGNC | 45 |
| MFIL ® | 1.5 |
| SCMC | 0.45 |
| GANTREZ ® S-97 | 0.75 |
| sodium lauryl sulphate | 2.5 |
| sodium Silicate (30%) | 1.75 |
| Flavour | 0.2 |
| triclosan ® | 0.3 |
| other minors to* | 100 |

*this includes preservative, benzyl alcohol, colour, pigments and sachharin.

The test method is as follows.

Test Method:

A panel test of twenty human volunteers was formed for the experiment. The test method is based on a method reported by R L Wijeijweera and I. Kleinberg in Archs. Oral Biol., Vol. 34, No. 1, 1989, pages 43-53.

About 5 ml of saliva was collected from each volunteer. A single pooled sample was prepared by mixing all the individual samples.

From the pooled sample, measured quantities of saliva were transferred to Greiner® tubes. The tubes were centrifuged for seven to eight minutes at 3500 rpm. Thereafter, the optical density (OD) of the supernatant was measured by a known method. The OD was adjusted to 2.0 using a 600 nm filter and using phosphate buffer.

Thereafter, about 3 g of toothpaste and 9 g water was added to a Greiner® tube. The contents of each tube were mixed for 30 minutes to get a suspension which was allowed to stand for about an hour to allow maximum amount of triclosan to be extracted. Thereafter, the sediment was vortexed and centrifuged for 5 minutes at 3500 rpm before being placed in a vial. The sediment suspension was vortexed and an aliquot of 1 ml was added to each tube. The analysis was conducted after one hour by following Mucin-coated HAP disk procedure described in US2010/0150849 A1 (International Specialty Products) and the results are shown in table 3.

TABLE 3

| | triclosan in slurry/ppm | triclosan in supernatant/ppm |
| --- | --- | --- |
| composition 8 | 4.8 | 15 |
| marketed competitor product | 1.9 | 12 |

Data in table-3 indicates a significant difference between the concentrations in the slurry and the supernatant. The preferred composition showed higher triclosan content in the supernatant, thereby indicating that there was more triclosan was released.

It should be understood that the specific forms of the invention herein illustrated and described are intended to be representative only as certain changes may be made therein without departing from the clear teachings of the disclosure.

Although the invention has been described with reference to specific embodiments, it will be appreciated by those skilled in the art that the invention may be embodied in many other forms.

The invention claimed is:

1. A toothpaste composition comprising:
   (i) 30 to 60 wt % a Calcium based abrasive, wherein the calcium based abrasive is chalk;
   (ii) a copolymer of vinylmethyl ether and maleic acid; and,
   (iii) a clay,
   wherein a ratio of said Calcium based abrasive to said copolymer of vinyl methyl ether and maleic anhydride is at least 1:0.0075 and a ratio of said Calcium based abrasive to said clay is at least 1:0.02.

2. The toothpaste composition as claimed in claim 1, wherein said clay is a smectite clay.

3. The toothpaste composition as claimed in claim 1, comprising 0.1 to 2 wt % copolymer of vinylmethyl ether and maleic acid.

4. The toothpaste composition as claimed in claim 1, comprising 0.2 to 3 wt % clay.

5. The toothpaste composition as claimed in claim 1, further comprising 0.1 to 2 wt % gum.

6. The toothpaste composition as claimed in claim 1, wherein viscosity of said composition is 80,000 to 500,000 cps.

7. A cosmetic method of promoting oral hygiene comprising a step of applying to the teeth an effective amount of a toothpaste composition as claimed in claim 1.

8. The toothpaste composition as claimed in claim 1, further comprising up to 2 wt % thickening silica.

* * * * *